United States Patent
Miyashita et al.

(10) Patent No.: US 8,409,414 B2
(45) Date of Patent: Apr. 2, 2013

(54) GAS SENSOR AND NITROGEN OXIDE SENSOR

(75) Inventors: Takeya Miyashita, Kasugai (JP); Sang Jae Lee, Ama-Gun (JP); Kunihiko Nakagaki, Nagoya (JP)

(73) Assignee: NGK Insulators, Ltd., Nagoya (JP)

(*) Notice: Subject to any disclaimer, the term of this patent is extended or adjusted under 35 U.S.C. 154(b) by 1060 days.

(21) Appl. No.: 12/349,707

(22) Filed: Jan. 7, 2009

(65) Prior Publication Data

US 2009/0120791 A1    May 14, 2009

Related U.S. Application Data

(63) Continuation of application No. PCT/JP2007/063821, filed on Jul. 11, 2007.

(30) Foreign Application Priority Data

Jul. 12, 2006   (JP) .................................. 2006-191277

(51) Int. Cl.
G01N 27/26    (2006.01)

(52) U.S. Cl. ........................................ 204/429; 204/424

(58) Field of Classification Search ............. 204/412, 204/426, 424, 429
See application file for complete search history.

(56) References Cited

U.S. PATENT DOCUMENTS

| | | | |
|---|---|---|---|
| 6,205,843 B1 | 3/2001 | Tanaka et al. | |
| 6,284,112 B1 * | 9/2001 | Kato et al. | 204/425 |
| 2002/0060151 A1 | 5/2002 | Kato et al. | |
| 2003/0136674 A1 | 7/2003 | Kato et al. | |
| 2003/0188968 A1 | 10/2003 | Naito et al. | |
| 2004/0154920 A1 * | 8/2004 | Schneider et al. | 204/431 |
| 2004/0231985 A1 | 11/2004 | Kato et al. | |
| 2006/0231397 A1 | 10/2006 | Nakagaki et al. | |

FOREIGN PATENT DOCUMENTS

| | | |
|---|---|---|
| JP | 11-237362 A1 | 8/1999 |
| JP | 2000-028576 A1 | 1/2000 |
| JP | 2000-214130 A1 | 8/2000 |
| JP | 2003-021613 A1 | 1/2003 |
| JP | 2004-003964 A1 | 1/2004 |
| JP | 2005-283240 A1 | 10/2005 |

* cited by examiner

*Primary Examiner* — Luan Van
*Assistant Examiner* — Louis Rufo
(74) *Attorney, Agent, or Firm* — Burr & Brown

(57) ABSTRACT

A gas sensor and nitrogen oxide sensor, which, when fitted to the exhaust system of an internal combustion engine, can suppress the influence of harmful substances contained in a measurement gas and can prevent the reduction in sensitivity over time. A harmful substance-trapping layer is formed at a gas inlet for introducing a to-be-measured gas from an external space into an internal space, and in a buffering space formed between diffusion resistance portions. In a trap-formed portion of a gas passage in which the harmful substance-trapping layer is formed, the measurement gas can pass in an amount of 80% or more of when the harmful substance-trapping layer is not formed in the trap-formed portion. A diffusion resistance is attained in the diffusion resistance portions; a harmful substance is trapped in the harmful substance-trapping layer; and the measurement gas is allowed to flow into a detection electrode side.

25 Claims, 7 Drawing Sheets

GAS SENSOR AND NITROGEN OXIDE SENSOR

BACKGROUND OF THE INVENTION

1. Field of the Invention

The present invention relates to a gas sensor for measurement of a particular gas component in a to-be-measured gas and, in particular, to a nitrogen oxide sensor for measurement of NOx as a to-be-measured gas component.

2. Description of the Related Art

Various measurement methods and measurement apparatuses have been developed in order to know the concentration of a particular gas component in a to-be-measured gas. For example, there is known a gas sensor of limit current type which uses an ion-conductive solid electrolyte. Further, as a method for measurement of NOx in a to-be-measured gas (e.g. a combustion gas), there is known a technique which uses a sensor comprising an oxygen ion-conductive solid electrolyte (e.g. zirconia) and a Pt electrode and a Rh electrode both formed on the solid electrolyte and measures an electromotive force between the two electrodes utilizing the reducing ability of Rh for NOx (for example, Patent Literature 1).

In such a sensor, the electromotive force changes greatly for the change in the concentration of oxygen in a combustion gas (a to-be-measured gas) but the change of the electromotive force is small for the change in the concentration of to-be-measured gas component (e.g. NOx); therefore, the measurement result of concentration tends to be influenced by various factors.

Patent Literature 1: JP-B-2000-28576

When such a gas sensor is fitted to the exhaust system of internal combustion engine (e.g. automotive engine) and the internal combustion engine is operated, there has been a problem that the sensitivity of gas sensor to to-be-measured gas component (e.g. NOx) reduces gradually. The present inventors investigated on the reasons therefor and, as a result, it was found that the harmful substances (e.g. Mg) contained in the exhaust gas of internal combustion engine have a large influence.

The aim of the present invention is to provide a gas sensor and a nitrogen oxide sensor, which, when fitted to, for example, the exhaust system of internal combustion engine, can suppress the influence of harmful substances (e.g. Mg) contained in a to-be-measured gas and can prevent the reduction in sensitivity with the increase in use time.

SUMMARY OF THE INVENTION

In order to achieve the above aim, the present invention provides a gas sensor for measuring the amount of a to-be-measured gas component in a to-be-measured gas present in an external space, which comprises:

a solid electrolyte which is in contact with an external space, an internal space formed inside the solid electrolyte, a diffusion resistance portion for introducing a to-be-measured gas from the external space via a gas inlet, at a given diffusion resistance, a pumping means which has an inner pumping electrode formed inside the internal space and an outer pumping electrode formed outside the internal space and which subjects the oxygen contained in the to-be-measured gas introduced from the external space, to a pumping treatment based on a controlling voltage applied between the two electrodes, a gas component-measuring means having a detection electrode, which electrode decomposes a to-be-measured gas component contained in the to-be-measured gas after the pumping treatment by the pumping means and measures the to-be-measured gas component contained in the to-be-measured gas, based on the oxygen generated by the decomposition, and a harmful substance-trapping layer made of a porous material capable of trapping a harmful substance, which is formed apart from and upstream of the detection electrode in a gas passage formed inside the solid electrolyte so as to enable the flowing of the to-be-measured gas.

In order to achieve the above aim, the present invention also provides a nitrogen oxide sensor for measuring the amount of a nitrogen oxide component in a to-be-measured gas present in an external space, which sensor comprises:

a main body made of an oxygen ion-conductive solid electrolyte, which is in contact with the external space, a first internal space formed in the solid electrolyte, communicating with an external space, an upstream-side diffusion resistance portion formed as a slit for introducing a to-be-measured gas into the first internal space at a given diffusion resistance, a pumping means which has a first, inside, pumping electrode formed inside the first internal space and a first, outside, pumping electrode formed outside the first internal space and which subjects the oxygen contained in the to-be-measured gas introduced from the external space, to a pumping treatment based on a controlling voltage applied between the two electrodes, to control the oxygen partial pressure in the first internal space to a given level at which NO is not decomposed substantially, a second internal space communicating with the first internal space, a downstream-side diffusion resistance portion formed as a slit for introducing the atmosphere subjected to the pumping treatment in the first internal space, into the second internal space at a given diffusion resistance, a gas component-measuring means which has a second, inside, pumping electrode formed inside the second internal space and a second, outside, pumping electrode formed outside the second internal space and further has a detection electrode for decomposing the NO contained in the atmosphere introduced from the first internal space, by either of catalysis and electrolysis and measuring the to-be-measured gas component in the to-be-measured gas based on the oxygen generated by the decomposition, and a harmful substance-trapping layer made of a porous material capable of trapping a harmful substance, which is formed apart from and upstream of the detection electrode in a gas passage formed inside the solid electrolyte so as to enable the flowing of the to-be-measured gas.

In the gas sensor and the nitrogen oxide sensor both of the present invention, the harmful substance-trapping layer can be formed specifically in a trap-formed portion of the gas passage so that the to-be-measured gas can pass in an amount of 80% or more of when the harmful substance-trapping layer is not formed in the trap-formed portion.

The harmful substance-trapping layer is preferably made of any of alumina, zirconia and magnesium aluminum spinel.

Also, the harmful substance-trapping layer can be formed at a gas inlet through which the to-be-measured gas is introduced from the external space into the internal space. Further, the diffusion resistance portion can be provided at a plurality of locations and the harmful substance-trapping layer can be formed between these diffusion resistance portions.

Or, the diffusion resistance portion can be formed as a slit and the harmful substance-trapping layer can be formed in the gas passage portion formed by the slit of the diffusion resistance portion.

In the above constitution, the harmful substance-trapping layer can be formed on a wall of the gas passage portion. In that case, the harmful substance-trapping layer is preferably made of a porous alumina material having a porosity of 10% to 70%. The harmful substance-trapping layer can have, in a gas-flowing direction, a length of at least two times the thickness of the gas passage portion. Further, the harmful substance-trapping layer can have a thickness of at least 1/10 of the thickness of the gas passage portion.

Meanwhile, the harmful substance-trapping layer can be formed by being filled in the gas passage portion. In that case, the harmful substance-trapping layer is preferably made of a porous alumina material having a porosity of 40% to 80%. Such a harmful substance-trapping layer can trap at least any of Si, P, Zn, Ca and Mg.

Further, the gas component-measuring means can be constituted as a pumping means for measurement which decomposes, by at least either of catalysis and electrolysis, the to-be-measured gas component contained in the to-be-measured gas after the pumping treatment by the pumping means and subjects the oxygen generated by the decomposition, to a pumping treatment, and the to-be-measured gas component in the to-be-measured gas can be measured based on a pumping current which flows in the pumping means for measurement based on the pumping treatment of the pumping means for measurement.

Or, the gas component-measuring means can be constituted as an oxygen partial pressure detection means which decomposes, by catalysis, the to-be-measured gas component contained in the to-be-measured gas after the pumping treatment by the pumping means and generates an electromotive force corresponding to a difference between the oxygen amount generated by the decomposition and the oxygen amount contained in a reference gas, and the to-be-measured gas component in the to-be-measured gas can be measured based on the electromotive force detected by the oxygen partial pressure detection means.

In the gas sensor and the nitrogen oxide sensor both of the present invention, a harmful substance in a to-be-measured gas is trapped by the harmful substance-trapping layer, whereby the reduction in sensitivity to to-be-measured gas component, caused by the harmful substance can be prevented. Therefore, the sensor of the present invention has high durability. Further, the harmful substance-trapping layer traps the harmful substance and, moreover, has a small influence on the flow amount of to-be-measured gas; therefore, the influence of the harmful substance-trapping layer on the diffusion resistance portion formed in the gas passage can be made small.

EXPLANATION OF SYMBOLS

1: gas sensor; 5: harmful substance-trapping layer; 12a: first substrate layer; 12b: second substrate layer; 12c: third substrate layer; 12d: first solid electrolyte layer; 12e: spacer layer; 12f: second solid electrolyte layer; 14: sensor element; 16: space for introduction of reference gas; 18: first chamber; 20: second chamber; 22: gas inlet; 23: buffering space; 26: first diffusion resistance portion; 27: second diffusion resistance portion; 28: third diffusion resistance portion; 30a and 30b: slits; 30k: wall between slits; 40: inner pumping electrode; 42: outer pumping electrode; 44: main pumping cell; 48: reference electrode; 50: oxygen partial pressure detection cell for control; 60: detection cell; 62: fourth diffusion resistance portion; 64; pumping cell for measurement; 66: DC electric source; 68: ammeter; 70: auxiliary pumping electrode; 72: auxiliary pumping cell; 74: DC electric source; 80: heater; 82: insulating layer; 160: voltmeter; 164: oxygen partial pressure detection cell for measurement

DETAILED DESCRIPTION OF THE INVENTION

The gas sensor according to the present invention is described below with reference to the accompanying drawings, on gas sensor embodiments used for measurement of, for example, oxides (e.g. $O_2$, NO, $NO_2$, $SO_2$, $CO_2$ and $H_2O$) contained in the exhaust gas of vehicle or in the air, or combustible gases (e.g. CO and $C_nH_m$). The present invention is not restricted to the following embodiments and may be subjected to changes, modifications and improvements as long as there is no deviation from the scope of the present invention.

Embodiment 1-1

Figure 1:
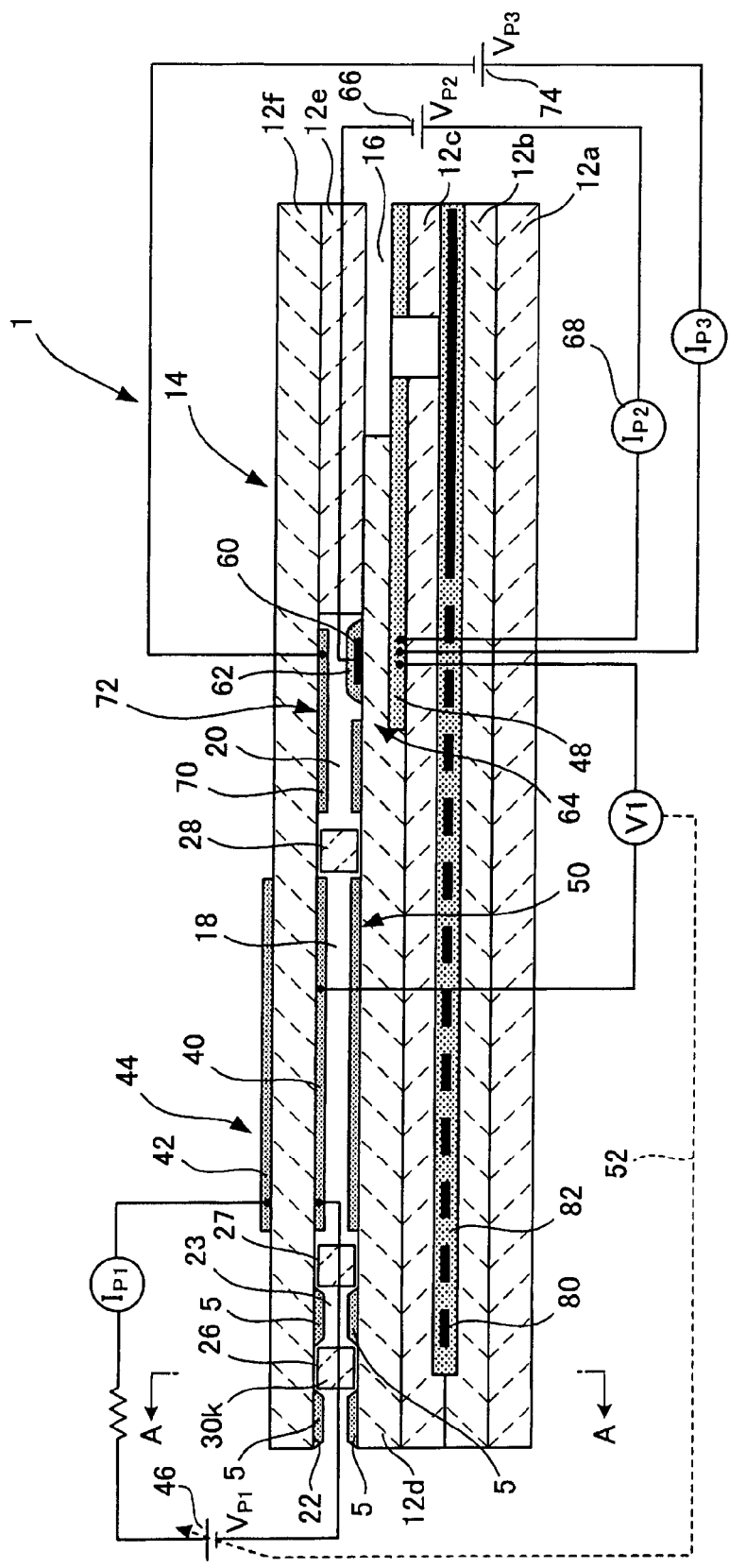
FIG. 1 is a sectional view showing a gas sensor according to the embodiment 1-1 of the present invention.

The gas sensor 1 according to the embodiment 1-1 has, as shown in FIG. 1, a sensor element 14 constituted by six (for example), laminated, solid electrolyte layers 12a to 12f made of a ceramic using an oxygen-conductive solid electrolyte such as $ZrO_2$ or the like.

In the sensor element 14, the first to third layers from below are a first substrate 12a, a second substrate layer 12b and a third substrate layer 12c, respectively; the fourth and sixth layers from below are a first solid electrolyte layer 12d and a second solid electrolyte layer 12f; and the fifth layer from below is a spacer layer 12e. Between the third substrate layer 12c and the spacer layer 12e, a space 16 for introduction of reference gas, into which a reference gas (e.g. air) used as a reference in oxide measurement is to be introduced, is surrounded and formed by the lower surface of the spacer layer 12e, the upper surface of the third substrate layer 12c and the side of the first solid electrolyte layer 12d.

Between the lower surface of the second solid electrolyte layer 12f and the upper surface of the first solid electrolyte layer 12d are formed a first chamber 18 which is a first internal space for adjusting the oxygen partial pressure in a to-be-measured gas, and a second chamber 20 which is a second internal space for finely adjusting the oxygen partial pressure in the to-be-measured gas and further measuring the oxide (e.g. nitrogen oxygen NOx) in the to-be-measured gas. A gas inlet 22 formed at the front end of the sensor element 14 and the first chamber 18 communicate with each other via a first diffusion resistance portion 26, a buffering space 23 and a second diffusion resistance portion 27; and the first chamber 18 and the second chamber 20 communicate with each other via a third diffusion resistance portion 28. A passage of to-be-measured gas extending from the gas inlet 22 to the second chamber 20 is called a gas passage.

Figure 2:
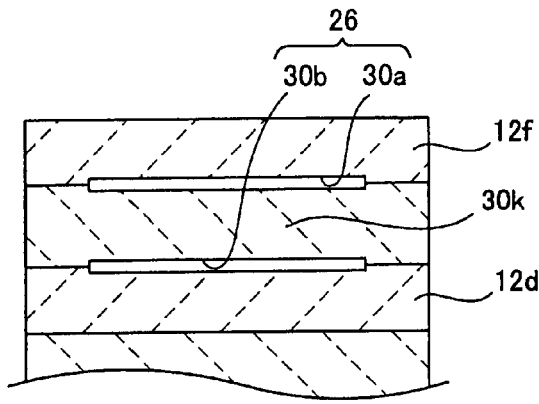
FIG. 2 is a A-A sectional view of FIG. 1.

Here, the first diffusion resistance portion 26 and the second diffusion resistance portion 27 are an upstream-side diffusion resistance portion; and the third diffusion resistance portion 28 is a downstream-side diffusion resistance portion to the to-be-measured gas introduced into the first chamber 18 and gives a given diffusion resistance to the to-be-measured gas introduced into the second chamber 20. As shown in FIG. 2 which is an A-A sectional view of FIG. 1, the first diffusion resistance portion 26 is formed by two oblong slits 30$a$ and 30$b$. Specifically explaining, the first diffusion resistance portion 26 is constituted by a slit 30$a$ which is formed by an oblong opening provided in contact with the lower surface of the second solid electrolyte layer 12$f$ so as to extend to the buffering space 23 at the same opening width, and a slit 30 $b$ which is formed by an oblong opening provided in contact with the upper surface of the first solid electrolyte layer 12$d$ so as to extend to the buffering space 23 at the same opening width.

In the embodiment 1-1, the slits 30$a$ and 30$b$ have about the same sectional shape of, for example, 10 μm or less in vertical direction length and about 2.5 mm in lateral direction length.

The second diffusion resistance portion 27 and the third diffusion resistance portion 28 are each formed as well by two oblong slits 30 $a$ and 30 $b$ having the same sectional shape as of the first diffusion resistance portion 26.

Between the first diffusion resistance portion 26 and the second diffusion resistance portion 27 is formed the buffering space 23 by being surrounded by the lower surface of the second solid electrolyte layer 12$f$ and the upper surface of the first solid electrolyte layer 12$d$. Owing to the pulsation of an exhaust gas in an external space, oxygen suddenly enters the sensor element through the gas inlet. This oxygen from the external space passes through the first diffusion resistance portion 26 and enters the buffering space 23. The sudden change of oxygen concentration caused by the pulsation of exhaust gas is cancelled by the buffering space 23 and the influence of the pulsation of exhaust gas in treatment space becomes substantially negligible.

The atmosphere in the first chamber 18 is introduced into the second chamber 20 through the third diffusion resistance portion 28 at a given diffusion resistance.

Figure 3A:
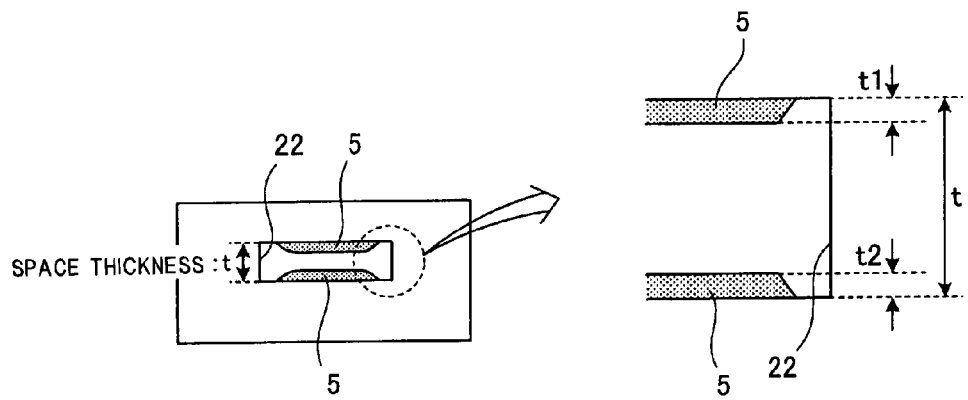
FIG. 3 is a view explaining a harmful substance-trapping layer.
Figure 3B:
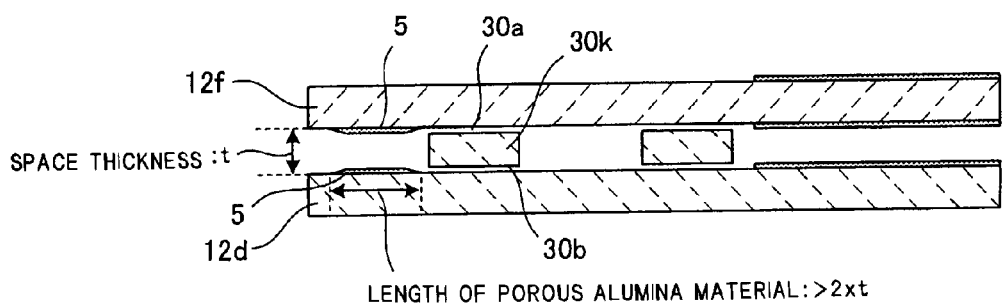

As shown in FIG. 1, FIG. 3($a$) and FIG. 3($b$), in a gas passage formed in the solid electrolyte and apart from and upstream of a detection electrode 60 is formed harmful substance-trapping layers 5 made of a porous material capable of trapping a harmful substance. Specifically explaining, In the embodiment 1-1 shown in FIG. 1, the harmful substance-trapping layers 5 are formed at the gas inlet 22 for introduction of to-be-measured gas from external space into internal space and also in the buffering space 23 formed between the diffusion resistance portions 26 and 27. These harmful substance-trapping layers 5 are formed on the walls forming the gas passage, specifically on the lower surface of the second solid electrolyte layer 12$f$ and on the upper surface of the first solid electrolyte layer 12$d$.

The harmful substance trapped by the harmful substance-trapping layers 5 refer to a substance contained in, for example, the exhaust gas of internal combustion engine, which has an influence on the reduction in the sensitivity of the gas sensor 1. It is, for example, Si, P, Zn, Ca or Mg. The harmful substance-trapping layers 5 can effectively remove, in particular, Mg (which has an influence on the reduction in sensitivity) from a to-be-measured gas.

As shown in FIG. 3($a$), the thickness (t1+t2) of each harmful substance-trapping layer 5 is preferably at least 1/10 of the thickness (space thickness) t of the gas passage because such a thickness makes large the volume of the layer 5 which functions for the trapping of harmful substance (e.g. Mg). Incidentally, the space thickness t is a length between the upper surface of the first solid electrolyte layer 12$d$ and the lower surface of the second solid electrolyte layer 12$f$. By employing such a constitution, the influence on the diffusion resistance is suppressed and yet the harmful substance such as Si, P, Zn, Ca, Mg or the like can be trapped.

As shown in FIG. 3($b$), the length of each harmful substance-trapping layer 5 in gas-flowing direction is made at least two times the thickness t of gas passage because the possibility of contact of harmful substance (e.g. Mg) with harmful substance-trapping layer 5 becomes high. By employing such a constitution, the influence on the diffusion resistance is suppressed and yet the harmful substance can be trapped. That is, by employing a constitution shown in FIG. 3($a$) and FIG. 3($b$), the to-be-measured gas can pass through a trap-formed portion of gas passage in which the harmful substance-trapping layer 5 is formed, in an amount of 80% or more of when the harmful substance-trapping layer 5 is not formed in the trap-formed region; a diffusion resistance can be attained in the diffusion resistance portion; and the harmful substance can be trapped in the harmful substance-trapping layer and the to-be-measured gas can be sent to a detection electrode 60 side. By thus constituting each harmful substance-trapping layer 5, the flow amount of to-be-measured gas in the trap-formed portion in which the harmful substance-trapping layer 5 is formed, is secured; thereby, the harmful substance can be trapped efficiently by the harmful substance-trapping layer 5. As a result, the present gas sensor, when fitted to, for example, the exhaust system of internal combustion engine and used, can suppress the influence of harmful substances contained in a to-be-measured gas and can prevent the reduction in sensitivity with the increase in use time.

Each harmful substance-trapping layer 5 is preferably made of any of alumina ($Al_2O_3$), zirconia ($ZrO_2$) and magnesium aluminum spinel ($MgAl_2O_4$). Desirably, the harmful substance-trapping layer 5 formed on the wall of gas passage is made of a porous alumina material having a porosity of 10% to 70%. More desirably, it is made of a porous alumina material having a porosity of 15% to 30%.

Back in FIG. 1, an inner pumping electrode 40 made of a flat, nearly rectangular, porous cermet electrode (e.g. a cermet electrode of Pt.$ZrO_2$ containing 1% of Au) is formed on the whole portion of the lower surface of the second solid electrolyte layer 12$f$, forming the first chamber 18; an outer pumping electrode 42 is formed on the portion of the upper surface of the second solid electrolyte layer 12$f$, corresponding to the inner pumping electrode 40; and an electrochemical pumping cell, that is, a main pumping cell (a pumping means) 44 is constituted by the inner pumping electrode 40, the outer pumping electrode 42 and the portion of second solid electrolyte layer 12$f$ sandwiched by the two electrodes 40 and 42.

Between the inner pumping electrode 40 and the outer pumping electrode 42, of the main pumping cell 44 is applied a required control voltage (a pumping voltage) Vp1 by an external variable electric source 46, to pass a pumping current Ip1 to a positive direction or a negative direction between the outer pumping electrode 42 and the inner pumping electrode 40; thereby, the oxygen in the atmosphere inside the first chamber 18 can be pumped out into an external space, or the oxygen in an external space can be pumped into the first chamber 18.

A reference electrode 48 is formed at a position opposing the detection electrode 60, which is sandwiched by the lower surface of the first solid electrolyte layer 12*d* and the third substrate layer 12*c*; and an electrochemical sensor cell, i.e. an oxygen partial pressure detection cell 50 for control is constituted by the inner pumping electrode 40, the reference electrode 48, the second solid electrolyte layer 12*f*, the spacer layer 12*e* and the first solid electrolyte layer 12*d*.

The oxygen partial pressure detection cell 50 for control can detect the oxygen partial pressure of the atmosphere in the first chamber 18 by the electromotive force V1 generated between the inner pumping electrode 40 and the reference electrode 48, based on the difference in oxygen concentration between the atmosphere of the first chamber 18 and the reference gas (air) in the space 16 for introduction of reference gas.

The oxygen partial pressure detected is used for feed back control of variable electric source 46. Specifically explaining, the pumping operation of main pumping cell 44 is controlled through a feed back control system 52 for main pump so that the oxygen partial pressure of the atmosphere in the first chamber 18 becomes a given value which is sufficiently low to conduct the control of oxygen partial pressure in the next second chamber 20.

This feed back control system 52 constitutes a circuit which feed back controls the pumping voltage Vp1 between the outer pumping electrode 42 and the inner pumping electrode 40 so that the difference between the potential of the inner pumping electrode 40 and the potential of the reference electrode 48 (i.e. detection voltage V1) becomes a given voltage level. In this case, the inner pumping electrode 40 is earthed.

Therefore, the main pumping cell 44 pumps out or pumps in the oxygen of the to-be-measured gas introduced into the first chamber 18, by an amount corresponding to the pumping voltage Vp1. By repeating a series of operations, the oxygen concentration in the first chamber 18 is feed back controlled to a desired level. In this state, the pumping current Ip1 flowing between the outer pumping electrode 42 and the inner pumping electrode 40 indicates a difference between the oxygen concentration in the to-be-measured gas and the controlled oxygen concentration in the first chamber 18 and can be used for measurement of the oxygen concentration in the to-be-measured gas.

Incidentally, the porous cermet electrode constituting each of the inner pumping electrode 40 and the outer pumping electrode 42 is constituted by a metal (e.g. Pt) and a ceramic (e.g. $ZrO_2$). However, the inner pumping electrode 40 which is provided in the first chamber 18 and which comes into contact with the to-be-measured gas, needs to be made of a material which is low in reduction ability for NO component of to-be-measured gas or has no such ability, and is preferably constituted, for example, by a compound of perovskite structure (e.g. $La_3CuO_4$), a cermet between a metal of low catalytic activity (e.g. Au) and a ceramic, or a cermet between a metal of low catalytic activity (e.g. Au), a Pt group metal and a ceramic. When an alloy between Au and a Pt group metal is used as the electrode material, the addition amount of Au is preferably 0.03 to 35 vol. % of the total metal components.

In the gas sensor 1 according to the embodiment 1-1, the detection electrode 60 made of a flat, nearly rectangular, porous cermet electrode is formed on the portion of the upper surface of the first solid electrolyte layer 12*d*, which forms the upper surface of the second chamber 20 and which is apart from the third diffusion resistance portion 28. So as to cover this detection electrode 60, there is formed an alumina film which constitutes a fourth diffusion resistance portion 62 and which is a porous protective layer for detection electrode. An electrochemical pumping cell, i.e. a pumping cell 64 for measurement is constituted by the detection electrode 60, the reference electrode 48 and the first solid electrolyte layer 12*d*.

The detection electrode 60 is constituted by a porous cermet composed of a metal capable of reducing NOx (a to-be-measured gas component) and zirconia (a ceramic), whereby it functions as a NOx reduction catalyst which reduces NOx present in the atmosphere of second chamber 20. In addition, the detection electrode 60 can pump out the oxygen in the atmosphere of second chamber 20, into the space 16 for introduction of reference gas, by applying a given voltage Vp2 between the detection electrode 60 and the reference electrode 48 via a DC electric source 66. The pumping current Ip2 which flows based on the pumping action of the pumping cell 64 for measurement, can be detected by an ammeter 68.

The given-voltage (DC) electric source 66 can apply such a voltage that can give a limit current to the pumping of the oxygen generated during the decomposition in the pumping cell 64 for measurement, in the NOx flow restricted by the fourth diffusion resistance portion 62.

Meanwhile, an auxiliary pumping electrode 70 made of a flat, nearly rectangular, porous cermet electrode (for example, a cermet electrode of Pt.$ZrO_2$ containing 1% of Au) is formed on the whole portion of the lower surface of the second solid electrolyte layer 12*f*, forming the second chamber 20; and an auxiliary electrochemical pumping cell, i.e. an auxiliary pumping cell 72 is constituted by the auxiliary pumping electrode 70, the second solid electrolyte layer 12*f*, the spacer layer 12*e*, the first solid electrolyte layer 12*d* and the reference electrode 48.

The auxiliary pumping electrode 70, like the inner pumping electrode 40 of the main pumping cell 44, is made of a material which is low in reduction ability for NO component of to-be-measured gas or has no such ability, and is preferably constituted, for example, by a compound of perovskite structure (e.g. $La_3CuO_4$), a cermet between a metal of low catalytic activity (e.g. Au) and a ceramic, or a cermet between a metal of low catalytic activity (e.g. Au), a Pt group metal and a ceramic. When an alloy between Au and a Pt group metal is used as the electrode material, the addition amount of Au is preferably 0.03 to 35 vol. % of the total metal components.

The oxygen in the atmosphere of the second chamber 20 can be pumped out into the space 16 for introduction of reference gas by applying a desired given voltage Vp3 between the auxiliary pumping electrode 70 and the reference electrode 48 both of the auxiliary pumping cell 72, using an external DC electric source 74.

Thereby, the oxygen partial pressure in the atmosphere of the second chamber 20 is controlled to a low level in which there is substantially no reduction or decomposition of to-be-measured gas component (NOx) and which gives substantially no influence on the measurement of the amount of target component. In this case, the change in oxygen amount introduced into second chamber 20 is made far smaller than the change in to-be-measured gas, by the action of the main pumping cell 44 in the first chamber 18, whereby the oxygen partial pressure in the second chamber 20 is controlled precisely at a given level.

Accordingly, in the gas sensor 1 according to the embodiment 1-1 having the above constitution, the to-be-measured gas whose oxygen partial pressure has been controlled in the second chamber 20, is introduced into the detection electrode 60.

Further, in the gas sensor 1 according to the embodiment 1-1, as shown in FIG. 1, a heater 80 which generates a heat when electrified from outside, is buried in a state that the heater 80 is sandwiched from above and below by the second substrate layer 12b and the third substrate layer 12c. The heater 80 is provided to enhance the conductivity of oxygen ion; and, on the upper and lower surfaces of the heater 80, an insulating layer (e.g. alumina) 82 is formed in order to obtain electrical insulation between the second substrate layer 12b and the third substrate layer 12c.

The heater 80 is provided so as to correspond to the whole portion extending from the first chamber 18 to the second chamber 20. Thereby, the first chamber 18 and the second chamber 20 are heated to respective given temperatures and, further, the main pumping cell 44, the oxygen partial pressure detection cell 50 for control and the pumping cell 64 for measurement are heated to respective given temperatures and maintained at the temperatures.

Next, description is made on the operation of the gas sensor 1 according to the embodiment 1-1. First, the front end side of the gas sensor 1 is provided in an external space, whereby a to-be-measured gas is introduced into the first chamber 18 via the first diffusion resistance portion 26 (slits 30a and 30b) and the second diffusion resistance portion 27 at given diffusion resistances. The to-be-measured gas introduced into the first chamber 18 undergoes the pumping action of oxygen, caused by applying a given pumping voltage Vp1 between the outer pumping electrode 42 and the inner pumping electrode 40 both constituting the main pumping cell 44; the oxygen partial pressure of the to-be-measured gas introduced is controlled at a given level, for example, $10^{-7}$ atm. This control is conducted using the feed back control system 52.

Incidentally, the first diffusion resistance portion 26 and the second diffusion resistance portion 27, when the pumping voltage Pp1 is applied to the main pumping cell 44, reduce the amount of the oxygen in the to-be-measured gas, which flows into the measurement space (the first chamber 18), and suppress the current flowing in the main pumping cell 44.

Also in the first chamber 18, even when it is heated by an external to-be-measured gas or further by the heater 80, there is formed such a state of oxygen partial pressure that the NOx in the atmosphere is not reduced by the inner pumping electrode 40 (there takes place no reaction of, for example, $NO \rightarrow \frac{1}{2}N_2 + \frac{1}{2}O_2$). The reason is that the reduction of NOx in the to-be-measured gas (the atmosphere) makes impossible the exact measurement of NOx in the next second chamber 20. Therefore, in the first chamber 18, it is necessary to form a state that NOx is not reduced by the component participating in the reduction of NOx (here, the metal component of the inner pimping electrode 40). Such a state can be achieved specifically by using, in the inner pumping electrode 40, a material low in reduction ability for NOx, for example, an alloy of Au and Pt, as mentioned above.

The gas in the first chamber 18 is introduced into the second chamber 20 through the third diffusion resistance portion 28 at a given diffusion resistance. The gas introduced into the second chamber 20 undergoes the oxygen-pumping action caused by applying a voltage Vp3 between the auxiliary pumping electrode 70 and the reference electrode 48 both constituting the auxiliary pumping cell 72, whereby the oxygen partial pressure of the gas is finely adjusted to become a given low level.

The third diffusion resistance portion 28, like the first diffusion resistance portion 26 and the second diffusion resistance portion 27, when the pumping voltage Vp3 is applied to the auxiliary pumping cell 72, reduces the amount of the oxygen in the to-be-measured gas, which flows into the measurement space (the second chamber 20), and suppresses the current Ip3 flowing in the auxiliary pumping cell 72.

The to-be-measured gas whose oxygen partial pressure has been controlled in the second chamber 20, as described above, is introduced into the detection electrode 60 through the fourth diffusion resistance portion 62 at a given diffusion resistance.

When the oxygen partial pressure of the atmosphere in the first chamber 18 is controlled to a low level which gives substantially no influence on the measurement of NOx, by operating the main pumping cell 44, in other words, the pumping voltage Vp1 of variable electric source 46 is adjusted, using the feed back control system 52, so that the voltage V1 detected by the oxygen partial pressure detection cell 50 for control becomes a given level and when the oxygen concentration in the to-be-measured gas changes largely in a range of, for example, 0 to 20%, the oxygen partial pressure of the atmosphere in the second chamber 20 and the oxygen partial pressure of the atmosphere around the detection electrode 60 ordinarily change slightly. This is considered to be because, when the oxygen concentration in to-be-measured gas becomes high, an oxygen concentration distribution appears in the width direction and thickness direction of the first chamber 18 and it changes correspondingly to the change of the oxygen concentration in to-be-measured gas.

However, in the gas sensor 1 according to the embodiment 1-1, the auxiliary pumping cell 72 is provided so that the oxygen partial pressure of the atmosphere in the second chamber 20 becomes a given low level always; therefore, even if the oxygen partial pressure of the atmosphere introduced from the first chamber 18 into the second chamber 20 has changed correspondingly to the oxygen concentration in to-be-measured gas, the oxygen partial pressure of the atmosphere in the second chamber 20 can be set at a given low level always by the pumping action of the auxiliary pumping cell 72 and, as a result, can be controlled to a low level which gives substantially no influence on the measurement of NOx.

The NOx of the to-be-measured gas introduced into the detection electrode 60 is reduced or decomposed around the detection electrode 60, and a reaction of, for example, $NO \rightarrow \frac{1}{2}N_2 + \frac{1}{2}O_2$ takes place. In this case, between the detection electrode 60 and the reference electrode 48 both constituting the pumping cell 64 for measurement, a given voltage Vp2 [for example, 430 mV (700° C.)] is applied in a direction in which oxygen is pumped out from the second chamber 20 into a reference gas-introducing space 16 side.

Therefore, the pumping current Ip2 flowing in the pumping cell 64 for measurement becomes a value which is proportional to the sum of the oxygen concentration in the atmosphere introduced into the second chamber 20, that is, the oxygen concentration in the second chamber 20 and the oxygen concentration generated by the reduction or decomposition of NOx by the detection electrode 60.

In this case, since the oxygen concentration in the atmosphere in the second chamber 20 is controlled at a given level by the auxiliary pumping cell 72, the pumping current Ip2 flowing in the pumping cell 64 for measurement is proportional to the concentration of NOx. Further, since this NOx concentration corresponds to the diffusion amount of NOx restricted by the fourth diffusion resistance portion 62, the NOx concentration can be measured accurately from the pumping cell 64 for measurement through the ammeter 68.

Thus, the pumping current Ip2 in the pumping cell 64 for measurement indicates mostly the amount of NOx reduction or decomposition and accordingly does not depend upon the oxygen concentration in to-be-measured gas.

As described above, in the gas sensor 1 according to the embodiment 1-1, the harmful substance-trapping layers 5 made of a porous material are formed apart from and upstream of the detection electrode 60, in the passage of to-be-measured gas inside the solid electrode, whereby a harmful substance can be trapped by the harmful substance-trapping layers and a to-be-measured gas can be sent to a detection electrode 60 side. Therefore, the present gas sensor 1, when fitted to, for example, the exhaust system of internal combustion engine and used, can suppress the influence of harmful substance contained in to-be-measured gas and can prevent the reduction in sensitivity with the increase in use time.

Embodiment 1-2

Figure 4:
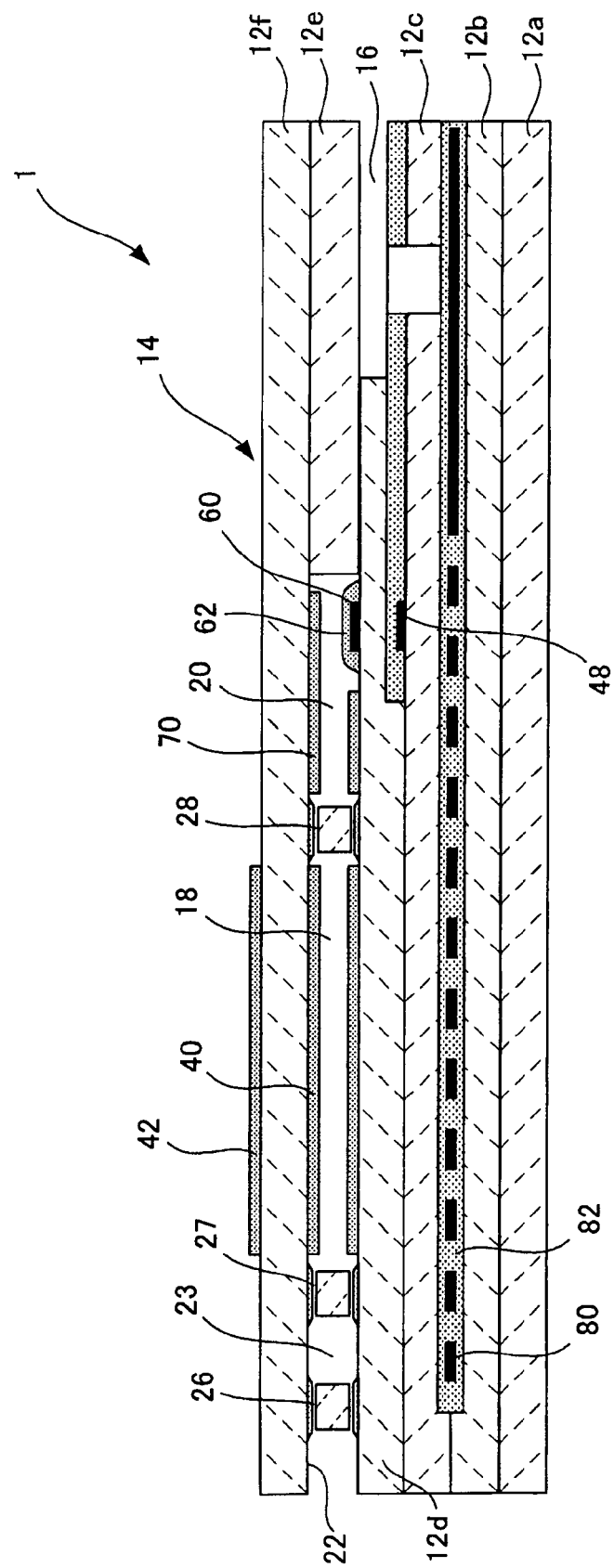
FIG. 4 is a sectional view showing a gas sensor according to the embodiment 1-2 of the present invention.

A gas sensor according to the embodiment 1-2 of the present invention is shown in FIG. 4. In the embodiment 1-2, a first diffusion resistance portion 26, a second diffusion resistance portion 27 and a third diffusion resistance portion 28 are formed as slits, and harmful substance-trapping layers are formed in the gas passage portions formed by the slits 30a and 30b of the diffusion resistance portions 26, 27 and 28.

Figure 5A:
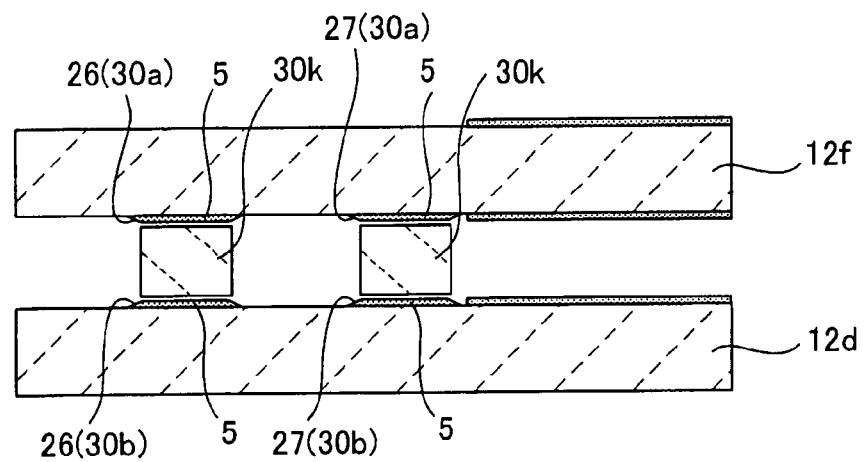
FIG. 5 is a partially enlarged view for explaining the harmful substance-trapping layer of FIG. 4.
Figure 5B:
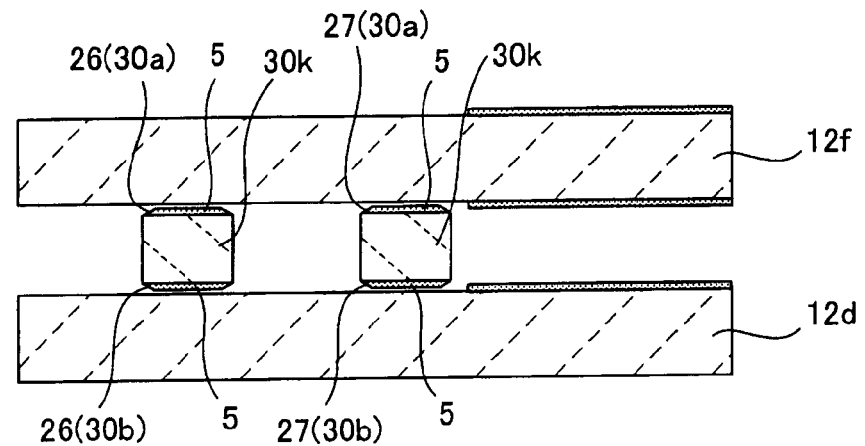

In FIG. 5(a) and FIG. 5(b) are shown partially enlarged views for explaining the harmful substance-trapping layers 5 of FIG. 4. As shown in FIG. 5(a), the harmful substance-trapping layers 5 are formed on the walls forming the gas passage portions, specifically on the lower surface of the second solid electrolyte layer 12f and on the upper surface of the first solid electrolyte layer 12d. Or, as shown in FIG. 5(b), the harmful substance-trapping layers 5 may be formed on the upper surface and lower surface of the wall 30k between slits sandwiched by the slits 30a and 30b. In both cases, each gas passage portion has therein a harmful substance-trapping layer 5 so that a space remains.

In the present embodiment 1-2, each harmful substance-trapping layer 5 is preferably made of any of alumina, $ZrO_2$ and magnesium aluminum spinel. Desirably, the harmful substance-trapping layer 5 formed so that a space remains in each slit, is made of a porous alumina material having a porosity of 10% to 70%. More desirably, it is made of a porous alumina material having a porosity of 15% to 30%.

Embodiment 1-3

Figure 6:
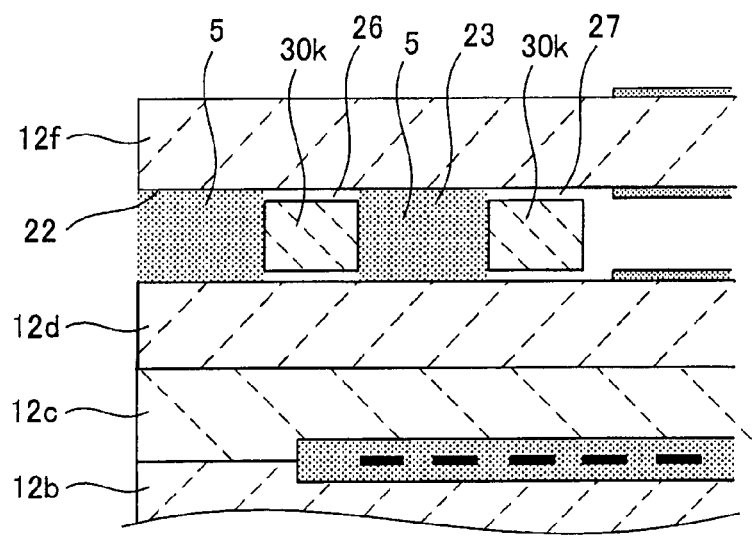
FIG. 6 is a sectional view showing a gas sensor according to the embodiment 1-3 of the present invention.

An embodiment 1-3 is shown in FIG. 6. In the embodiment shown in FIG. 6, harmful substance-trapping layers 5 are formed in a gas inlet 22 through which a to-be-measured gas is introduced from an external space into an internal space, and in a buffering space 23 formed between diffusion resistance portions 26 and 27. The harmful substance-trapping layers 5 formed in respective locations are formed by being filled in a gas passage.

The harmful substance-trapping layers 5 formed by being filled in a gas passage are desirably formed of a porous alumina material having a porosity of 40% to 80%, in order to secure the flow of to-be-measured gas. By forming the harmful substance-trapping layers 5 in this way, the flow amount of to-be-measured gas can be secured, a harmful substance can be trapped, and the to-be-measured gas can be sent to a detection electrode 60 side. Thus, the present embodiment 1-3, when fitted to, for example, the exhaust system of internal combustion engine and used, can suppress the influence of the harmful substance contained in the to-be-measured gas and can prevent the reduction in sensitivity with the increase in use time.

Embodiment 1-4

Figure 7:
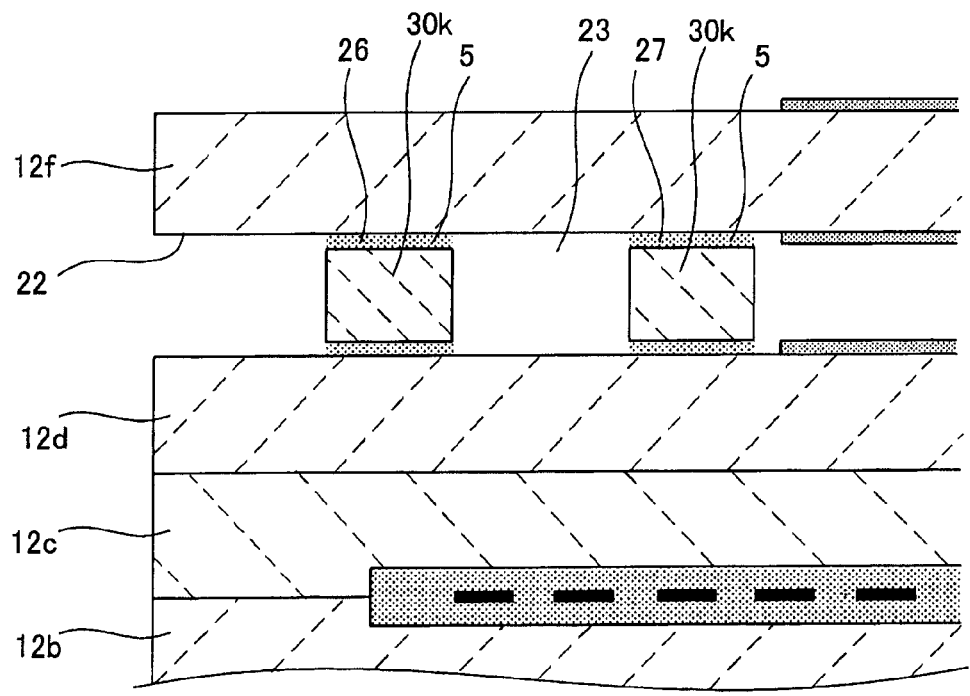
FIG. 7 is a sectional view showing a gas sensor according to the embodiment 1-4 of the present invention.

Further, an embodiment 1-4 is shown in FIG. 7. In the embodiment 1-4, a first diffusion resistance portion 26, a second diffusion resistance portion 27 and a third diffusion resistance portion 28 are formed as slits, and harmful substance-trapping layers 5 are formed by being filled in gas passage portions formed by the slits of diffusion resistance portions. As shown in FIG. 7, each harmful substance-trapping layer 5 is formed on the walls forming each gas passage portion in each slit; specifically between the lower surface of a second solid electrolyte layer 12f and the upper surface of a wall 30k between slits, or between the upper surface of a first solid electrolyte layer 12d and the lower surface of a wall 30k between slits. In this case, each harmful substance-trapping layer 5 is formed in each gas passage portion so that no space remains in the gas passage portion.

The harmful substance-trapping layers 5 formed so that no space remains, are desirably formed by a porous alumina material having a porosity of 40% to 80%, in order to secure the flow of to-be-measured gas. By forming the harmful substance-trapping layers 5 in this way, the flow amount of to-be-measured gas can be secured, a harmful substance can be trapped, and the to-be-measured gas can be sent to a detection electrode 60 side. Thus, the present embodiment 1-4, when fitted to, for example, the exhaust system of internal combustion engine and used, can suppress the influence of the harmful substance contained in the to-be-measured gas and can prevent the reduction in sensitivity with the increase in use time.

Embodiment 2

Figure 8:
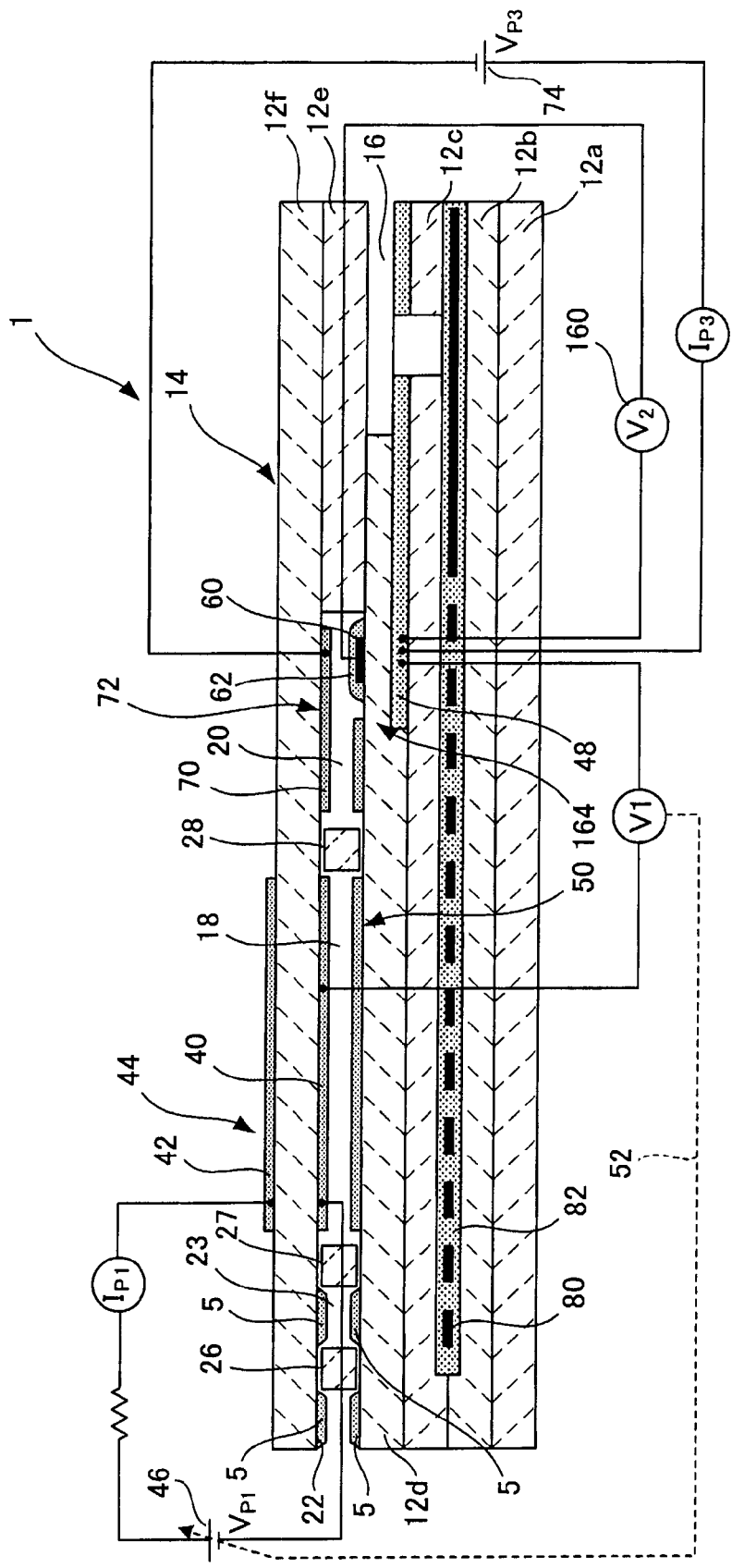
FIG. 8 is a sectional view showing a gas sensor according to the embodiment 2 of the present invention.

Next, description is made on a gas sensor 1 according to the embodiment 2 of the present invention, with reference to FIG. 8. Incidentally, the sensor components corresponding to those of FIG. 1 are given the same signals, and repeated explanation of these signals is not made.

As shown in FIG. 8, a gas sensor 1 according to the embodiment 2 has about the same constitution as the gas sensor 1 (see FIG. 1) according to the embodiment 1-1, but is different in that an oxygen partial pressure detection cell 164 for measurement is provided in place of the pumping cell 64 for measurement.

The oxygen partial pressure detection cell 164 for measurement is constituted by a detection electrode 60 formed on the portion of the upper surface of a first solid electrolyte layer 12d, forming a second chamber 20, a reference electrode 48 formed on the lower surface of the first solid electrolyte layer 12d, and the first solid electrolyte layer 12d sandwiched by the two electrodes 60 and 48.

In this case, between the detection electrode 60 and the reference electrode 48, of the oxygen partial pressure detection cell 164 for measurement is generated an electromotive force (an electromotive force of oxygen concentration cell) V2 which corresponds to the difference in oxygen concentration between the atmosphere around the detection electrode 60 and the atmosphere around the reference electrode 48.

Therefore, by measuring the electromotive force (voltage) V2 generated between the detection electrode 60 and the reference electrode 48 by a voltmeter 160, an oxygen partial pressure around the detection electrode 60, in other words, an oxygen partial pressure specified by the oxygen generated by reduction or decomposition of to-be-measured gas component (NOx) can be detected as a voltage V2.

By employing such a constitution, the flow amount of to-be-measured gas can be secured, a harmful substance can be trapped, and the to-be-measured gas can be sent to a detection electrode 60 side. Thus, the present embodiment 2, when fitted to, for example, the exhaust system of internal combustion engine and used, can suppress the influence of the harmful substance contained in the to-be-measured gas and can prevent the reduction in sensitivity with the increase in use time.

EXAMPLES

In order to confirm the effect of the above-described sensor of the present invention, the present sensor and a conventional sensor provided with no harmful substance-trapping layer 5 were examined for the change in NOx sensitivity with the increase in use time. The test results of the present invention and the conventional technique are shown in FIG. 9.

Figure 9:
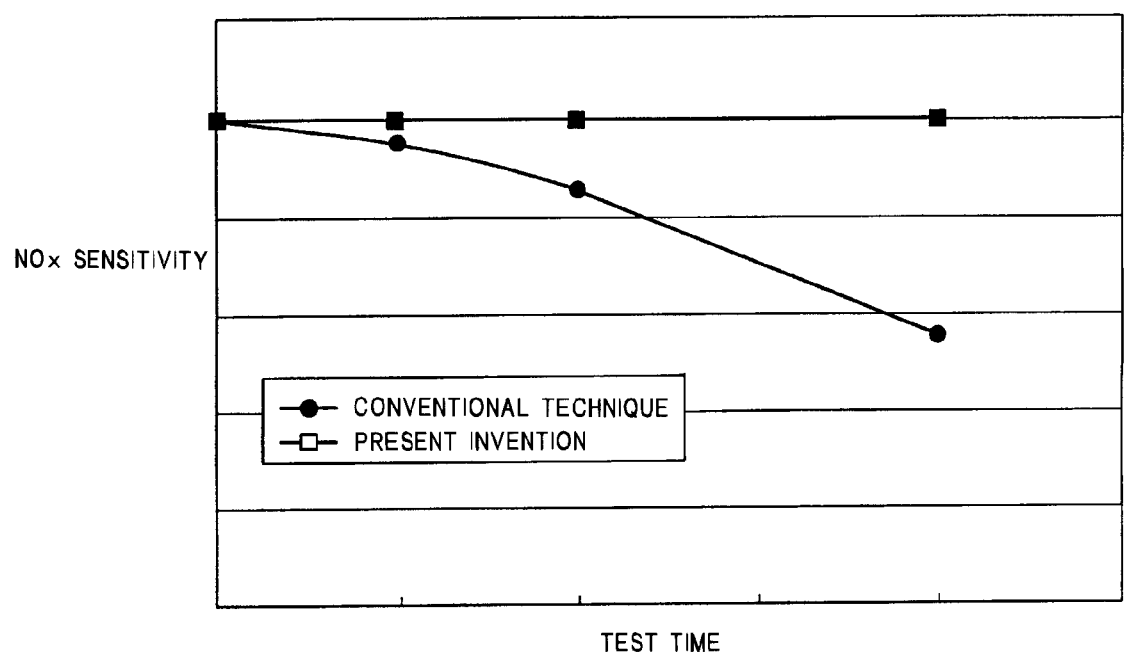
FIG. 9 is a view showing the test results of the present invention and a conventional technique.

As shown in FIG. 9, in the present invention, harmful substance is trapped by the harmful substance-trapping layer 5, whereby the influence of harmful substance contained in to-be-measured gas can be suppressed and the reduction in sensitivity with the increase in use time can be prevented.

In the gas sensors 1 (including modification cases) according to the embodiments 1 and 2, oxygen and NOx were selected as to-be-measured gas components; however, these gas sensors can be effectively used as well to the measurement of bound oxygen-containing gas components (e.g. $H_2O$ and $CO_2$) other than NOx, which is influenced by the oxygen present in to-be-measured gas.

The gas sensors can also be used, for example, in a gas sensor in which the $O_2$ generated by electrolysis of $CO_2$ or $H_2O$ is pumped out by an oxygen pump, or in a gas sensor in which the $H_2$ generated by electrolysis of $H_2O$ is subjected to a pumping treatment using a proton-conductive solid electrolyte.

In the above, cases having first to fourth diffusion resistance portions were described. However, the number of diffusion resistance portions formed is not restricted thereto. Cases having diffusion resistance portions as slits were also described. The present invention is applicable also to a case having diffusion resistance portions other than slits, made of, for example, a porous material.

INDUSTRIAL APPLICABILITY

The gas sensor and nitrogen oxide sensor of the present invention can be used as a sensor fitted to, for example, the exhaust system of internal combustion engine.

The invention claimed is:

1. A gas sensor for measuring an amount of a to-be-measured gas component in a to-be-measured gas present in an external space, which comprises:
   a solid electrolyte which is in contact with an external space,
   an internal space formed inside the solid electrolyte,
   a first diffusion resistance portion and a second diffusion resistance portion for introducing the to-be-measured gas from the external space via a gas inlet, at a given diffusion resistance,
   a pumping means which has an inner pumping electrode formed inside the internal space and an outer pumping electrode formed outside the internal space and which subjects the oxygen contained in the to-be-measured gas introduced from the external space, to a pumping treatment based on a controlling voltage applied between the two electrodes,
   a gas component-measuring means having a detection electrode, which electrode decomposes the to-be-measured gas component contained in the to-be-measured gas after the pumping treatment by the pumping means and measures the to-be-measured gas component contained in the to-be-measured gas, based on the oxygen generated by the decomposition,
   a porous protective layer for detection electrode, which is formed so as to cover the detection electrode of the gas component-measuring means, and
   a harmful substance-trapping layer made of a porous material capable of trapping a harmful substance, which is formed apart from and upstream of the detection electrode, in a gas passage formed inside the solid electrolyte so as to enable the flowing of the to-be-measured gas, wherein the harmful substance-trapping layer is in contact with at least an upper surface of the gas passage and a lower surface of the gas passage, which are directly opposed to each other, and extends between the gas inlet and the first diffusion resistance portion and between the first diffusion resistance portion and the second diffusion resistance portion.

2. A gas sensor according to claim 1, wherein the harmful substance-trapping layer is formed in a trap-formed portion of the gas passage so that the to-be-measured gas can pass in an amount of 80% or more of when the harmful substance-trapping layer is not formed in the trap-formed portion.

3. A gas sensor according to claim 1, wherein the harmful substance-trapping layer is made of any of alumina, zirconia and magnesium aluminum spinel.

4. A gas sensor according to claim 1, wherein the harmful substance-trapping layer is formed on a wall of the gas passage portion.

5. A gas sensor according to claim 4, wherein the harmful substance-trapping layer is made of a porous alumina material having a porosity of 10% to 70%.

6. A gas sensor according to claim 4, wherein the harmful substance-trapping layer has, in a gas-flowing direction, a length of at least two times the thickness of the gas passage portion.

7. A gas sensor according to claim 4, wherein the harmful substance-trapping layer has a thickness of at least 1/10 of the thickness of the gas passage portion.

8. A gas sensor according to claim 1, wherein the harmful substance-trapping layer is formed by being filled in the gas passage portion.

9. A gas sensor according to claim 8, wherein the harmful substance-trapping layer is made of a porous alumina material having a porosity of 40% to 80%.

10. A gas sensor according to claim 1, wherein the harmful substance-trapping layer traps at least any of Si, P, Zn, Ca and Mg.

11. A gas sensor according to claim 1, wherein
    the gas component-measuring means is constituted as a pumping means for measurement which decomposes, by at least either of catalysis and electrolysis, the to-be-measured gas component contained in the to-be-measured gas after the pumping treatment by the pumping means and subjects the oxygen generated by the decomposition, to a pumping treatment, and
    the to-be-measured gas component in the to-be-measured gas is measured based on a pumping current which flows in the pumping means for measurement based on the pumping treatment of the pumping means for measurement.

12. A gas sensor according to claim 1, wherein
    the gas component-measuring means is constituted as an oxygen partial pressure detection means which decomposes, by catalysis, the to-be-measured gas component contained in the to-be-measured gas after the pumping treatment by the pumping means and generates an electromotive force corresponding to a difference between the oxygen amount generated by the decomposition and the oxygen amount contained in a reference gas, and the to-be-measured gas component in the to-be-measured gas is measured based on the electromotive force detected by the oxygen partial pressure detection means.

13. A nitrogen oxide sensor for measuring an amount of a nitrogen oxide component in a to-be-measured gas present in an external space, which sensor comprises:

a main body made of an oxygen ion-conductive solid electrolyte, which is in contact with the external space, a first internal space formed in the solid electrolyte, communicating with an external space via a gas inlet, an upstream-side diffusion resistance portion formed as a slit for introducing the to-be-measured gas into the first internal space at a given diffusion resistance, a pumping means which has a first, inside, pumping electrode formed inside the first internal space and a first, outside, pumping electrode formed outside the first internal space and which subjects the oxygen contained in the to-be-measured gas introduced from the external space, to a pumping treatment based on a controlling voltage applied between the two electrodes, to control the oxygen partial pressure in the first internal space to a given level at which NO is not decomposed substantially, a second internal space communicating with the first internal space, a downstream-side diffusion resistance portion formed as a slit for introducing the atmosphere subjected to the pumping treatment in the first internal space, into the second internal space at a given diffusion resistance, a gas component-measuring means which has a second, inside, pumping electrode formed inside the second internal space and a second, outside, pumping electrode formed outside the second internal space and further has a detection electrode for decomposing the NO contained in the atmosphere introduced from the first internal space, by either of catalysis and electrolysis and measuring the to-be-measured gas component in the to-be-measured gas based on the oxygen generated by the decomposition, a porous, protective layer for detection electrode, formed so as to cover the detection electrode of the gas component-measuring means, and a harmful substance-trapping layer made of a porous material capable of trapping a harmful substance, which is formed apart from and upstream of the detection electrode, in a gas passage formed inside the solid electrolyte so as to enable the flowing of the to-be-measured gas, wherein the harmful substance-trapping layer is in contact with at least an upper surface of the gas passage and a lower surface of the gas passage, which are directly opposed to each other, and extends between the gas inlet and the upstream-side diffusion resistance portion and between the upstream-side diffusion resistance portion and the downstream-side diffusion resistance portion.

14. A nitrogen oxide sensor according to claim 13, wherein the harmful substance-trapping layer is formed in a trap-formed portion of the gas passage so that the to-be-measured gas can pass in an amount of 80% or more of when the harmful substance-trapping layer is not formed in the trap-formed portion.

15. A nitrogen oxide sensor according to claim 13, wherein the harmful substance-trapping layer is made of any of alumina, zirconia and magnesium aluminum spinel.

16. A nitrogen oxide sensor according to claim 13, wherein the diffusion resistance portions are each formed as a slit and the harmful substance-trapping layer is formed in the gas passage portion formed by the slit of each diffusion resistance portion.

17. A nitrogen oxide sensor according to claim 13, wherein the harmful substance-trapping layer is formed on a wall of the gas passage portion.

18. A nitrogen oxide sensor according to claim 17, wherein the harmful substance-trapping layer is made of a porous alumina material having a porosity of 10% to 70%.

19. A nitrogen oxide sensor according to claim 17, wherein the harmful substance-trapping layer has, in a gas-flowing direction, a length of at least two times the thickness of the gas passage portion.

20. A nitrogen oxide sensor according to claim 17, wherein the harmful substance-trapping layer has a thickness of at least 1/10 of the thickness of the gas passage portion.

21. A nitrogen oxide sensor according to claim 13, wherein the harmful substance-trapping layer is formed by being filled in the gas passage portion.

22. A nitrogen oxide sensor according to claim 21, wherein the harmful substance-trapping layer is made of a porous alumina material having a porosity of 40% to 80%.

23. A nitrogen oxide sensor according to claim 13, wherein the harmful substance-trapping layer traps at least any of Si, P, Zn, Ca and Mg.

24. A nitrogen oxide sensor according to claim 13, wherein
the gas component-measuring means is constituted as a pumping means for measurement which decomposes, by at least either of catalysis and electrolysis, the to-be-measured gas component contained in the to-be-measured gas after the pumping treatment by the pumping means and subjects the oxygen generated by the decomposition, to a pumping treatment, and the to-be-measured gas component in the to-be-measured gas is measured based on a pumping current which flows in the pumping means for measurement based on the pumping treatment of the pumping means for measurement.

25. A nitrogen oxide sensor according to claim 13, wherein
the gas component-measuring means is constituted as an oxygen partial pressure detection means which decomposes, by catalysis, the to-be-measured gas component contained in the to-be-measured gas after the pumping treatment by the pumping means and generates an electromotive force corresponding to a difference between the oxygen amount generated by the decomposition and the oxygen amount contained in a reference gas, and the to-be-measured gas component in the to-be-measured gas is measured based on the electromotive force detected by the oxygen partial pressure detection means.

* * * * *